(12) United States Patent
Nagasaka

(10) Patent No.: US 11,226,219 B2
(45) Date of Patent: Jan. 18, 2022

(54) FLUID MEASUREMENT APPARATUS, FLUID MEASUREMENT METHOD, AND PROGRAM

(71) Applicant: KYOCERA Corporation, Kyoto (JP)

(72) Inventor: Yushi Nagasaka, Otsu (JP)

(73) Assignee: KYOCERA Corporation, Kyoto (JP)

(*) Notice: Subject to any disclaimer, the term of this patent is extended or adjusted under 35 U.S.C. 154(b) by 0 days.

(21) Appl. No.: 16/964,104

(22) PCT Filed: Jan. 23, 2019

(86) PCT No.: PCT/JP2019/002148
§ 371 (c)(1),
(2) Date: Jul. 22, 2020

(87) PCT Pub. No.: WO2019/146663
PCT Pub. Date: Aug. 1, 2019

(65) Prior Publication Data
US 2021/0041274 A1    Feb. 11, 2021

(30) Foreign Application Priority Data
Jan. 23, 2018   (JP) .............................. JP2018-008501

(51) Int. Cl.
*G01F 1/66* (2006.01)
(52) U.S. Cl.
CPC .................................... *G01F 1/661* (2013.01)
(58) Field of Classification Search
CPC ........................................................ G01F 1/661
See application file for complete search history.

(56) References Cited

U.S. PATENT DOCUMENTS 3,866,055 A * 2/1975 Pike ..................... G01S 17/50
250/564
3,941,477 A * 3/1976 Schodl .................. G01F 1/661
356/28

(Continued)

FOREIGN PATENT DOCUMENTS

EP           3045876 A1    7/2016
JP        2015-132580 A    7/2015

(Continued)

OTHER PUBLICATIONS

Translation of WO-2015033469-A1 (Year: 2015).*

*Primary Examiner* — Nathaniel T Woodward
(74) *Attorney, Agent, or Firm* — Procopio, Cory, Hargreaves & Savitch LLP

(57) ABSTRACT

A fluid measurement apparatus according to an embodiment includes an optical emitter capable of radiating light to an irradiation target including a fluid, an optical detector capable of receiving scattered light scattered by the fluid, and a controller that includes a generator configured to generate a frequency spectrum based on the scattered light and an estimation unit configured to estimate a flow state of the fluid, based on a characteristic component of the frequency spectrum. The controller causes the generator to generate a first frequency spectrum based on a measurement target fluid and a second frequency spectrum based on the fluid in a known flow state, and then causes the estimation unit to compare a characteristic component of the first spectrum and a characteristic component of the second frequency spectrum, whereby the controller can estimate a flow state of the measurement target fluid.

13 Claims, 8 Drawing Sheets

(56) References Cited

U.S. PATENT DOCUMENTS

| | | | | |
|---|---|---|---|---|
| 6,261,233 B1 * | 7/2001 | Kantorovich | ............ | A61B 8/06 |
| | | | | 600/454 |
| 6,874,480 B1 * | 4/2005 | Ismailov | ................ | F02M 65/00 |
| | | | | 123/494 |
| 7,657,392 B2 * | 2/2010 | Gysling | ................ | G01N 9/002 |
| | | | | 702/128 |
| 7,736,314 B2 * | 6/2010 | Beach | ................ | G01S 7/52026 |
| | | | | 600/437 |
| 9,127,975 B2 * | 9/2015 | Jordan | .................... | G01F 1/666 |
| 2008/0225264 A1 * | 9/2008 | Melnyk | ................... | G01F 1/661 |
| | | | | 356/28 |
| 2012/0002189 A1 * | 1/2012 | Bengoechea Apezteguia | ............ | |
| | | | | G01S 17/58 |
| | | | | 356/28.5 |

FOREIGN PATENT DOCUMENTS

| | | | |
|---|---|---|---|
| JP | 2017-113320 A | 6/2017 | |
| WO | 2015/033469 A1 | 3/2015 | |
| WO | WO-2015033469 A1 * | 3/2015 | ............ G01F 1/661 |
| WO | 2017/174977 A1 | 10/2017 | |

\* cited by examiner

FLUID MEASUREMENT APPARATUS, FLUID MEASUREMENT METHOD, AND PROGRAM

CROSS REFERENCE TO RELATED APPLICATION

This application claims priority to and the benefit of Japanese Patent Application No. 2018-8501 filed on Jan. 23, 2018, the entire contents of which are incorporated herein by reference.

TECHNICAL FIELD

The present disclosure relates to a fluid measurement apparatus, a fluid measurement method, and a program.

BACKGROUND

Conventionally, apparatuses for measuring a flow rate or a flow velocity of a flowing object are known. For example, PTL 1 set forth below describes an apparatus that optically measures a flow rate.

CITATION LIST

Patent Literature

PTL 1: JP-A-2017-113320

SUMMARY

A fluid measurement apparatus according to an embodiment includes an optical emitter capable of radiating light to an irradiation target including a fluid, an optical detector capable of receiving scattered light scattered by the fluid, a generator configured to generate a frequency spectrum based on the scattered light, and an estimation unit configured to estimate a flow state of the fluid based on a characteristic component of the frequency spectrum. The controller causes the generator to generate a first frequency spectrum based on a measurement target fluid and a second frequency spectrum based on the fluid in a known flow state, and then causes the estimation unit to compare a characteristic component of the first frequency spectrum and a characteristic component of the second frequency spectrum, whereby the controller can estimate a flow state of the measurement target fluid.

A fluid measurement method according to an embodiment includes a step of radiating light to an irradiation target including a fluid and a flow path in which the fluid flows, a step of receiving scattered light scattered by the fluid, a step of generating a frequency spectrum based on the scattered light, and a step of estimating a flow state of the fluid based on a characteristic component of the frequency spectrum. The fluid measurement method according to the includes generating a first frequency spectrum based on a measurement target fluid and a second frequency spectrum based on the fluid in a known flow state and then comparing a characteristic component of the first frequency spectrum and a characteristic component of the second frequency spectrum, whereby the fluid measurement method can estimate a flow state of the measurement target fluid.

A program according to an embodiment causes a computer to execute a step of radiating light to an irradiation target including a fluid and a flow path in which the fluid flows, a step of receiving scattered light scattered by the fluid, a step of generating a frequency spectrum based on the scattered light, and a step of estimating a flow state of the fluid based on a characteristic component of the frequency spectrum. The program according to the embodiment causes the computer to generate a first frequency spectrum based on a measurement target fluid and a second frequency spectrum based on the fluid in a known flow state, and then to compare a characteristic component of the first frequency spectrum and a characteristic component of the second frequency spectrum, whereby the program can cause the computer to estimate a flow state of the measurement target fluid.

DETAILED DESCRIPTION

A fluid measurement apparatus capable of measuring a flow state of a fluid under various conditions can improve the convenience. The present disclosure relates to provision of highly convenient fluid measurement apparatus, fluid measurement method, and program. According to an embodiment, highly convenient fluid measurement apparatus, fluid measurement method, and program can be provided. Hereinafter, the embodiment of the present disclosure will be described with reference to the drawings. First, a configuration of the fluid measurement apparatus according to the embodiment will be described.

Figure 1:
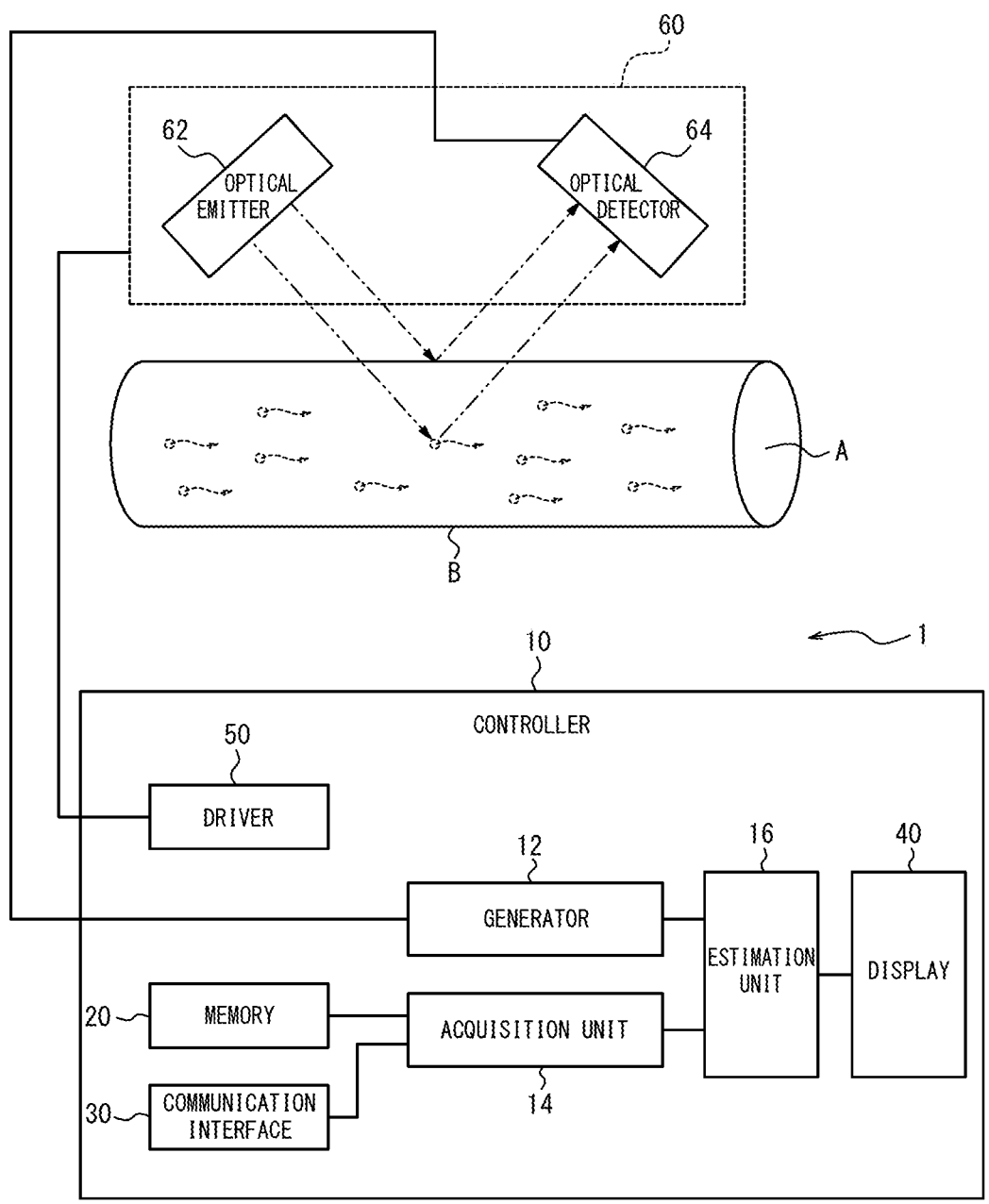
FIG. 1 is block diagram illustrating an example schematic configuration of a fluid measurement apparatus according to an embodiment.

FIG. 1 is a block diagram illustrating an example schematic configuration of the fluid measurement apparatus according to the embodiment.

FIG. 1 is a block diagram illustrating functional units included in the fluid measurement apparatus according to the embodiment. Note that FIG. 1 schematically illustrates a fluid A flowing through a flow path B. Further, a power source configured to supply electric power to each functional unit, a configuration for supplying electric power to each functional unit from the power source, and the like are omitted.

The fluid measurement apparatus according to the embodiment can calculate a flowing state (a flow state) of a flowing object (a fluid). In particular, the fluid measurement apparatus can calculate a flow rate or a flow velocity of the fluid as the flow state of the fluid. The flow rate is a volume or mass of the fluid flowing per unit time, and the flow velocity is a travel distance of the fluid per unit time.

The fluid measurement apparatus can calculate the flow state of the fluid by utilizing the Doppler effect on light. Light radiated to an irradiation target (i.e., a fluid, a flow path of the fluid, etc.) is scattered by the fluid, and its frequency is shifted (Doppler shift) due to the Doppler effect, in accordance with the flow state of the fluid. Thus, the flow state can be calculated using the Doppler effect. In particular, the fluid measurement apparatus can cause an optical emitter to radiate light to an irradiation target including a measurement target fluid and cause an optical detector to receive interference light including light scattered by the irradiation target. Then, the fluid measurement apparatus can calculate the flow state of the fluid, based on output of the optical detector.

The measurement target fluid may be any fluid whose flow state can be calculated using the Doppler effect on light. In particular, the fluid may be any fluid that scatters light per se or that flows a substance that scatters light (a scattering substance). The fluid may be, for example, water, blood, printer ink, or a powder-containing gas. When the scattering substance or powder are flown in a fluid, the fluid measurement apparatus can regard a flow rate or flow velocity of the scattering substance or powder as the flow rate or flow velocity of the fluid. That is, the "fluid flow rate or flow velocity" can also be interpreted as the "flow rate or flow velocity of the scattering substance or powder".

The fluid measurement apparatus 1 according to the embodiment includes a controller 10 configured to control the fluid measurement apparatus 1. In the fluid measurement apparatus 1 according to the embodiment, a sensor 60 is configured to perform detection associated with the fluid A flowing through the flow path B. In the fluid measurement apparatus 1, the controller 10 can estimate the flow state of the fluid A flowing through the flow path B, based on a result of the detection by the sensor 60.

A position of the sensor 60 may be determined with respect to the flow path B in such a manner as to be able to estimate the flow state of the fluid A flowing through the flow path B. The sensor 60 includes an optical emitter 62 and an optical detector 64.

The optical emitter 62 can radiate light to the flow path B. The optical emitter 62 can radiate, for example, laser light. The optical emitter 62 may radiate, as measurement light, laser light having a wavelength capable of detecting a specific component, such as the fluid A or a solid contained in the fluid A. The optical emitter 62 is configured using, for example, any number of LDs (Laser Diodes).

The optical emitter 62 simply needs to be driven by a driver 50 of the controller 10. The driver 50 simply needs to be configured using any laser drive circuit or the like. The driver 50 may be provided external to the fluid measurement apparatus 1 or built in the sensor 60. As a result, the fluid measurement apparatus 1 can improve the degree of design freedom.

The optical detector 64 can receive light scattered by the fluid A after being radiated from the optical emitter 62. Further, the optical detector 64 can receive light scattered by the flow path B after being radiated from the optical emitter 62. That is, the optical detector 64 can receive interference light including light scattered by the fluid A and light scattered by the flow path B. The optical detector 64 is configured using, for example, any number of PDs (Photo Diodes).

A signal (an optical signal) related to light received by the optical detector 64 is transmitted to a generator 12 of the controller 10. The generator 12 will be described later. In transmitting the optical signal of light received by the optical detector 64 to the generator 12 for processing, various amplifiers and/or filters may be used (not illustrated).

Note that the sensor 60 is not limited to the configuration illustrated in FIG. 1. For example, the sensor 60 may include the optical emitter 62 and the optical detector 64 that are independent of each other, rather than including them as a package. As a result, the fluid measurement apparatus 1 can increase the degree of design freedom and improve the convenience.

Next, the controller 10 of the fluid measurement apparatus 1 will be described.

The controller 10 of the fluid measurement apparatus 1 includes the generator 12, an acquisition unit 14, and an estimation unit 16. The controller 10 may further include at least one of a memory 20, a communication interface 30, a display 40, and the driver 50, as appropriate.

The controller 10 includes at least one processor such as, for example, a CPU (Central Processing Unit) configured to provide control and processing capabilities for executing various functions of the generator 12, the acquisition unit 14, and the estimation unit 16. The controller 10 may realize the functions of the generator 12, the acquisition unit 14, the estimation unit 16, and the like as one processor in a collective manner, a plurality of processors, or discrete processors. The processor may be realized as an integrated circuit (IC: Integrated Circuit) or a discrete circuit. The processor simply needs to be realized based on various other known technologies. In one embodiment, the functions of the generator 12, the acquisition unit 14, and the estimation unit 16 to be executed by the controller 10 may be configured as, for example, a CPU and a program to be executed by the CPU.

The generator 12 can generate a frequency spectrum, based on output of the optical detector 64 of the sensor 60, and output the frequency spectrum to the estimation unit 16. The acquisition unit 14 can retrieve a frequency spectrum stored in the memory 20 and output the frequency spectrum to the estimation unit 16. The estimation unit 16 can estimate the flow state of the fluid A, based on the frequency spectrum generated by the generator 12 and the frequency spectrum retrieved by the acquisition unit 14.

The memory 20 may be configured using a semiconductor memory, a magnetic memory, or the like. The memory 20 can store various types of information, programs to be executed, and the like. The memory 20 may also function as a working memory of the acquisition unit 14 and/or the estimation unit 16. The memory 20 can further store a frequency spectrum. The memory 20 may preliminarily store a frequency spectrum generated by the generator 12 or a frequency spectrum externally acquired via communication or the like. The memory 20 may be various types of memory cards or the like.

The communication interface 30 can realize various communication functions including wireless communication. The communication interface 30 may realize communication by employing various communication systems including, for example, LTE (Long Term Evolution). The communication interface 30 may include a modem whose communication system is standardized by, for example, ITU-T (International Telecommunication Union Telecommunication Standardization Sector). The communication interface 30 may wirelessly communicate with an external apparatus such as, for example, an external server or a cloud server via a network using, for example, an antenna. In one embodiment, the communication interface 30 may receive a second frequency spectrum S2 from an external database such as, for example, an external server or a cloud server. The second frequency spectrum S2 received by the communication interface 30 may be stored in the memory 20.

The display 40 can display various information such as a measurement result of the flow state of the fluid A on various display devices to notify a user. The display device may be a liquid crystal display (LCD), an organic EL (Eelectroluminescent) display, an inorganic EL display, or the like. The display 40 may display a character, a figure, a symbol, an image including a graph, or the like. The display 40 may also display an image such as an operation object or the like.

Information notified by the display 40 to the user is not necessarily limited to one that gives the user a visual effect. For example, the display 40 may output a sound indicating various kinds of information that can notify the user accordingly.

The memory 20, the communication interface 30, and the display 40 of the controller 10 may be incorporated in the fluid measurement apparatus 1 or may be provided external to the fluid measurement apparatus 1. Further, for example, the display 40 may be built in the sensor 60. As a result, the fluid measurement apparatus can improve the degree of design freedom.

The flow path B through which the fluid A flows may be any tubular member formed from various materials. In particular, the flow path B simply needs to be formed from a material that transmits at least a part of light radiated by the optical emitter 62. The material of the flow path B may be, for example, plastic, vinyl chloride, glass, or the like. Further, the flow path B may be, for example, a body tissue such as the blood vessel or the like in which human/animal body fluid flows. The flow path B simply needs to be formed preventing leakage of the fluid A, in a manner to allow appropriate measurement of the flow state of the fluid A.

Figure 2:
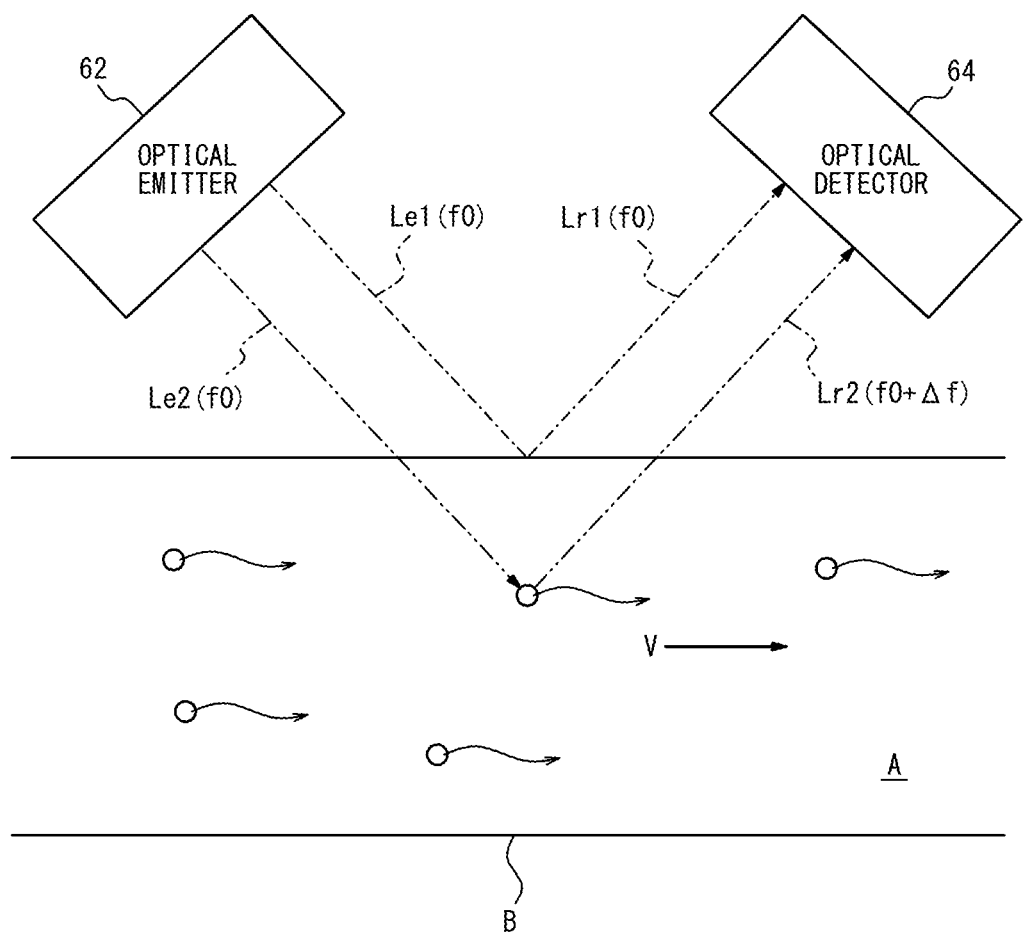
FIG. 2 is a diagram illustrating detection of interference light performed by the fluid measurement apparatus according to an embodiment.

Next, detection of scattered light performed in fluid measurement according to an embodiment will be described. FIG. 2 is a diagram illustrating the detection of scattered light performed in the fluid measurement according to the embodiment.

FIG. 2 is a diagram illustrating detection of the interference light by the fluid measurement apparatus according to the embodiment. In FIG. 2, the fluid A contains scattering substances, some of which are indicated by white circles, for the convenience of explanation. In FIG. 2, the scattering substances are flowing to the right at a velocity V.

Light radiated to the flow path B from the optical emitter 62 includes incident light Le1 and incident light Le2. When the incident light Le1 and the incident light Le2 are radiated from the optical emitter 62, they have a frequency f0. The incident light Le1 having the frequency f0 will be referred to as Le1 (f0), and the incident light Le2 having the frequency f0 will be referred to as Le2 (f0).

The incident light Le1 undergoes interface reflection on the surface of the flow path B, which is stationary. That is, the incident light Le1 is not scattered by the fluid A but scattered by the surface of the flow path B. The incident light Le1 is scattered by the surface of the flow path B and transformed into scattered light Lr1. The scattered light Lr1 is formed by the incident light Le1 scatted by the surface of the stationary flow path B. At this time, since the flow path B is stationary and the Doppler effect does not occur, the incident light Le1 maintains the frequency f0. The scattered light Lr1 having the frequency f0 will be referred to as Lr1 (f0).

The incident light Le2 passes through the surface of the flow path B without undergoing interface reflection on the surface of the flow path B. That is, the incident light Le2 is not scattered by the surface of the flow path B but scattered by the fluid A. The incident light Le2 is scattered by the fluid A and transformed into scattered light Lr2. At this time, since the incident light Le2 is scattered by the fluid A, the frequency f0 is subjected to the Doppler shift. The scattered light Lr2 in which the frequency f0 changes by a frequency Δf will be expressed by Lr2(f0+Δf).

The optical detector 64 receives the scattered light Lr1 and the scattered light Lr2 described above. Thus, the fluid measurement apparatus 1 can estimate the flow state of the fluid A using output of the optical detector 64 as one element.

Figure 3:
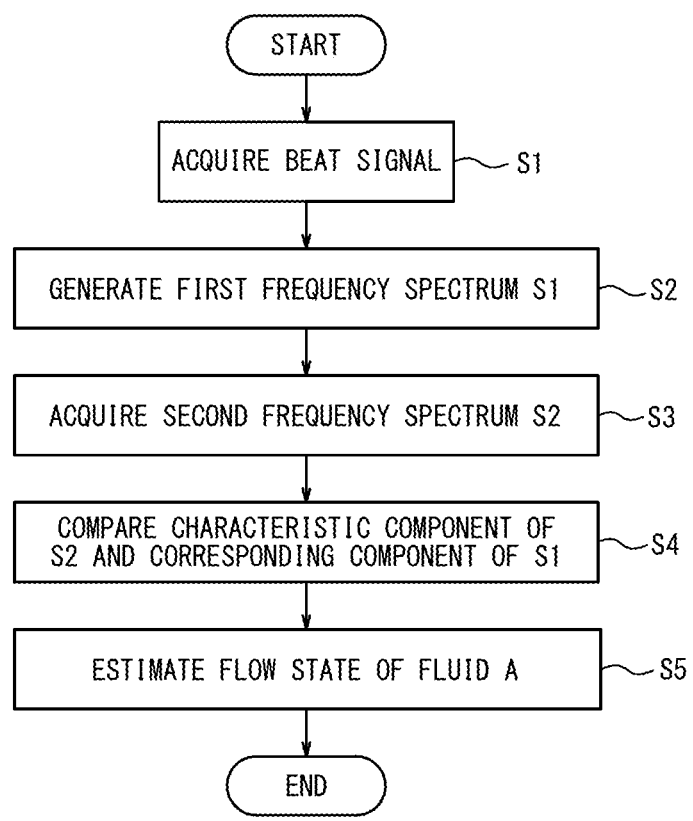
FIG. 3 is an example flowchart to be executed by the fluid measurement apparatus according to an embodiment.

FIG. 3 illustrates an example flowchart of flow state estimation to be executed by the controller 10 of the fluid measurement apparatus 1 according to an embodiment.

First, the generator 12 acquires a beat signal of interference light caused by interference between the scattered light Lr1 from the stationary flow path B and the scattered light Lr2 from the fluid A serving as a measurement target (step S1). The beat signal indicates a relationship between a beat intensity and time.

Figure 4:
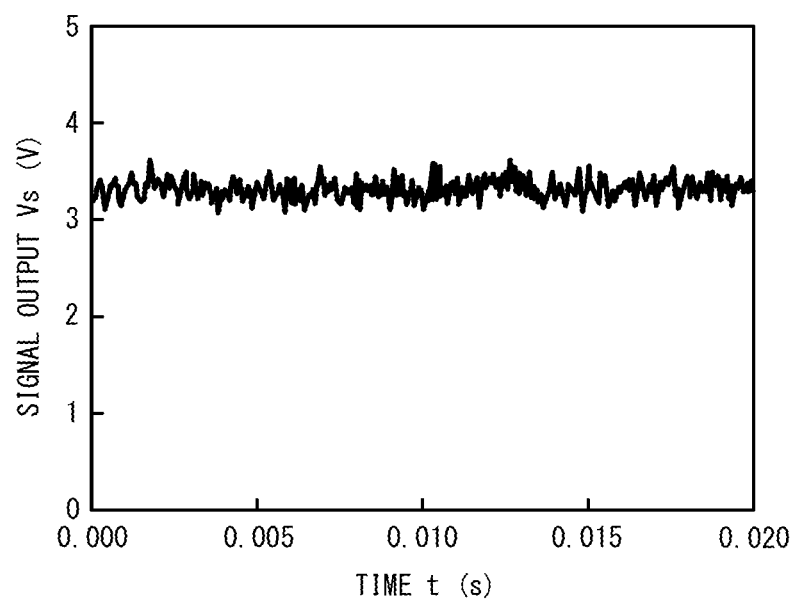
FIG. 4 is a diagram for explaining a principle of fluid measurement according to an embodiment.

FIG. 4 is a diagram illustrating an example of the beat signal acquired in step S1 of FIG. 3. In FIG. 4, the vertical axis represents a signal output intensity, and the horizontal axis represents time. In the example illustrated in FIG. 4, a signal output from the optical detector 64 is a voltage value, represented by a signal output Vs in the unit of voltage (V). The beat signal is not limited to the voltage and may be anything that indicates a temporal change in the signal output intensity. The signal output may be, for example, a current value or a resistance value.

Next, the generator 12 generates the frequency spectrum (a first frequency spectrum) S1 on the basis of the measuring target fluid, based on an acquired beat signal (step S2). The frequency spectrum is a spectrum that indicates a relationship between a frequency f included in the beat signal and an intensity P(f) of each frequency. The generator 12 can generate the frequency spectrum by performing the fast Fourier transform (FFT) on the beat signal acquired in step S1.

Figure 5:
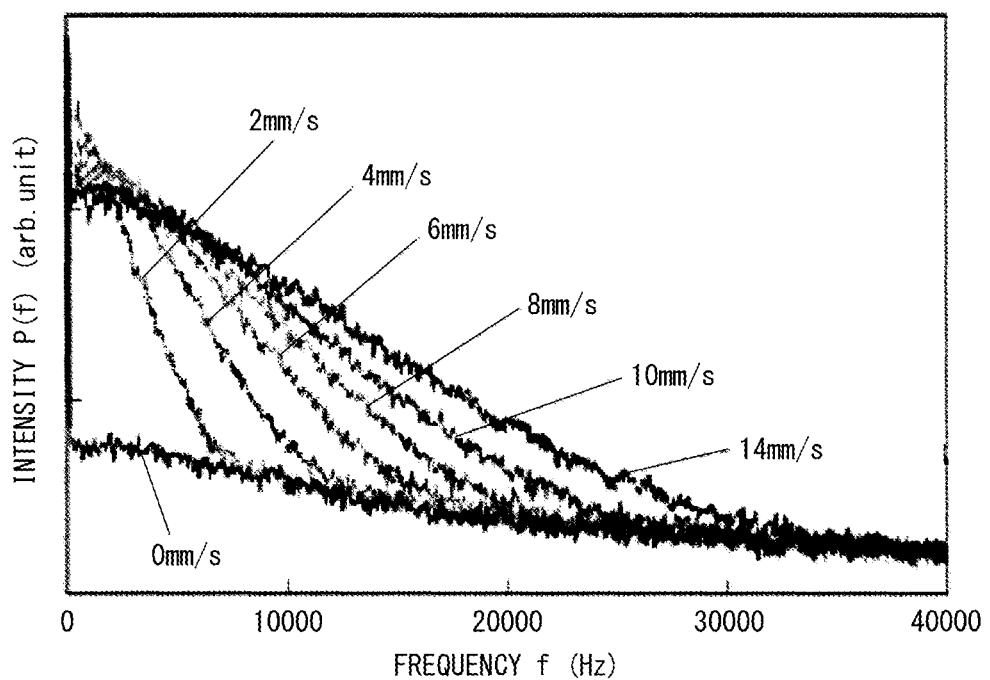
FIG. 5 is a diagram for explaining a principle of fluid measurement according to an embodiment.

FIG. 5 is a diagram illustrating an example of the frequency spectrum. In FIG. 5, the vertical axis represents the intensity P(f) in an arbitrary unit, and the horizontal axis represents the frequency f. In FIG. 5, the frequency spectrums corresponding to flow velocities of the fluid A at 2 mm/s, 4 mm/s, 6 mm/s, 8 mm/s, 10 mm/s, and 14 mm/s are illustrated by way of example.

In the frequency spectrum, the higher the flow velocity of the fluid A, the higher the intensity of the frequency on a high frequency side. The fluid measurement apparatus 1 can estimate the flow state of the fluid, based on such a change in the frequency spectrum.

The estimation unit 16 can perform frequency weighting on the frequency spectrum P(f) (formula (1)). That is, a product of each frequency f and its intensity P(f) can be calculated.

[Formula 1]

$$f \cdot P(f) \tag{1}$$

The estimation unit 16 can calculate an integrated value set forth below by integrating the above formula (1) in an appropriate frequency range (formula (2)):

[Formula 2]

$$\int f \cdot P(f) df \tag{2}$$

The estimation unit 16 multiplies the integral value obtained by the above formula (2) by a proportional constant K. Then, the estimation unit 16 performs normalization by dividing a resulting value by a total power ($I^2$) of the received light signal, i.e., a DC component, so as not to depend on the intensity of the received light such as laser light. Thus, the following value can be calculated (Formula (3)):

[Formula 3]

$$\frac{K \int f \cdot P(f) df}{I^2} \quad (3)$$

The estimation unit 16 can estimate the flow state of the measurement target fluid by comparing a calculated value of the formula (3) of the measurement target fluid with a value of the formula (3) calculated by preliminarily measuring the fluid in a known flow state.

Figure 6:
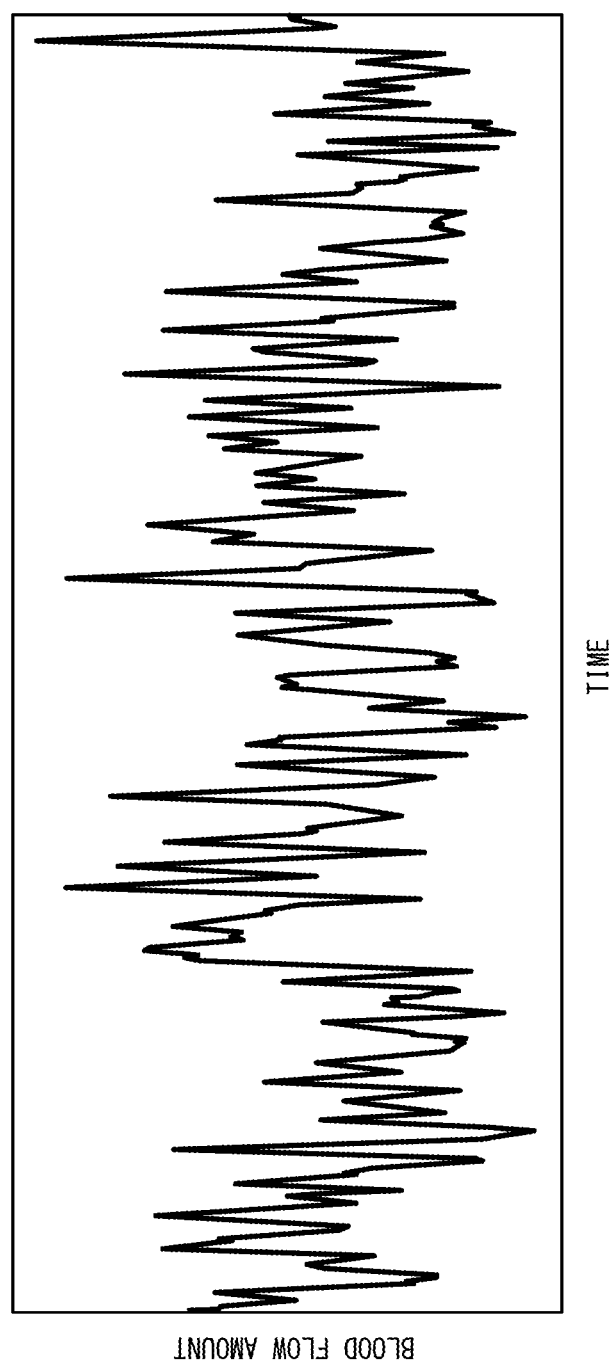
FIG. 6 is a diagram for explaining a principle of fluid measurement according to an embodiment.

FIG. 6 is a diagram illustrating an example flow rate of the fluid estimated by the fluid measurement apparatus 1 according to an embodiment. FIG. 6 illustrates a change in an amount of blood flowing in the blood vessel, i.e., a temporal change in the blood flow amount, by way of example. The blood flow amount indicated by the vertical axis is in an arbitrary unit.

Here, depending on the measurement environment and the like, the frequency spectrum may include an unintended noise. Thus, measurement without eliminating the influence of a noise reduces the measurement accuracy. On the other hand, the fluid measurement apparatus 1 according to the embodiment can estimate the fluid flow state, based on a component (a characteristic component) characteristic of each fluid flow state included in the frequency spectrum P(f). As a result, the fluid measurement apparatus 1 can reduce the influence of various noises, and thus can improve an estimation accuracy. That is, the fluid measurement apparatus 1 can improve the convenience.

Further, a flow meter that utilizes the principle of the Doppler shift may detect fluctuations in a radiation level of laser light as a noise. Thus, the intensity indicated by the frequency spectrum is the sum of the scattered light component of a slow fluid and a deviated laser component. That is, the measurement accuracy is deteriorated. On the other hand, the fluid measurement apparatus 1 according to the embodiment can reduce the influence of a noise and thus improve the estimation accuracy.

Also, an upper limit of a frequency axis when performing FFT analysis depends on a sampling rate. Thus, an amount of the Doppler shift of the frequency exceeding the upper limit of the frequency of the FFT analysis is not observed. That is, the measurement accuracy is reduced as the flow rate or flow velocity of the fluid increases. On the other hand, the fluid measurement apparatus 1 can estimate the flow state of the fluid, based on various characteristic components and thus improve the estimation accuracy.

A magnitude of the flow rate of the fluid also depends on a cross-sectional area of the flow path. That is, a fluid in the same flow rate flows fast in a thin channel and flows slow in a wide channel. For this reason, it has been difficult to measure a flow rate if a cross-sectional area of the flow channel is unknown. On the other hand, the fluid measurement apparatus 1 according to the embodiment can estimate the flow rate without necessarily using information regarding the cross-sectional area of the flow channel. That is, the fluid measurement apparatus 1 can improve the convenience.

Further, the fluid measurement apparatus 1 according to the embodiment can perform non-invasive measurement and thus improve the convenience.

Hereinafter, fluid measurement performed by the fluid measurement apparatus 1 according to an embodiment will be further described.

The acquisition unit 14 of the fluid measurement apparatus 1 can retrieve the frequency spectrum S2 (the second frequency spectrum) on the basis of a fluid in a known flow state, which is to be compared with the first frequency spectrum S1 retrieved in step S2, from the memory 20 (step S3). In this case, the fluid measurement apparatus 1 may preliminarily measure the fluid in the known flow state and store the relationship between the known flow state and the second frequency spectrum S2 generated by the generator 12 in the memory 20. In step S3, further, the fluid measurement apparatus 1 may store the second frequency spectrum S2 in an external apparatus such as an external server or a cloud server via the communication interface 30. In this case, the acquisition unit 14 may retrieve the second frequency spectrum S2 via the communication interface 30. The fluid measurement apparatus 1 can reduce an actual measurement time by preliminarily storing the second frequency spectrum S2 in the memory 20 or the like. That is, the fluid measurement apparatus 1 can improve the convenience.

The known flow state may be grasped by any appropriate method. The known flow state may be grasped using, for example, another flow meter such as a thermal flow meter or an eddy current flow meter, or a pump capable of flowing a fluid at a determined flow rate.

The fluid measurement apparatus 1 may store the frequency spectrum together with various measurement conditions that realize the frequency spectrum. The measurement conditions may include, for example, algorithm conditions such as a sampling rate and an ADC conversion rate, or measurement environment conditions such as a temperature and an atmospheric pressure. Also, the fluid measurement apparatus 1 may appropriately record intensity variance of the optical emitter 62 configured using the LD, the frequency of light radiated by the optical emitter 62, the positional relationship between the flow path B and the sensor 60, the cross-sectional area of the flow path B, a material and texture of the material forming the flow path B, an expected experimental environment noise, and the like. As a result, the fluid measurement apparatus 1 can reduce the influence of a measurement error caused by a difference in the measurement conditions and thus improve the estimation accuracy.

The stored second frequency spectrum S2 and various variables that realize the spectrum may be appropriately updated on a regular or irregular basis by acquiring information from an external server or the like via the communication interface 30 or the like. As a result, the fluid measurement apparatus 1 can appropriately select a condition suitable for measurement and thus improve the convenience.

The estimation unit 16 compares a characteristic component S1c of the first frequency spectrum S1 with a characteristic component S2c of the second frequency spectrum S2 (step S4). The acquisition unit 14 can select and acquire a second frequency spectrum S2 that has a characteristic component suitable for comparison with the characteristic component S1c of the first frequency spectrum S1.

The estimation unit 16 may estimate the flow state of the fluid A by adopting a second frequency spectrum S2 corresponding to a minimum value of a formula (4) set forth below and comparing the second frequency spectrum S2 with the first frequency spectrum S1. As a result, the fluid measurement apparatus 1 can improve the estimation accuracy. In the formula (4), one of F and f may be a value based on the first frequency spectrum S1, and the other one may be a value based on the second frequency spectrum S2.

[Formula 4]

$$\sum_{i}^{N} \left( \frac{F_i}{F_{i+1}} - \frac{f_i}{f_{i+1}} \right)^2 \quad (4)$$

Further, the estimation unit 16 may add an intensity of an average frequency of the frequency spectrum as a variable to the formula (4). The intensity of the average frequency may be calculated by the following formula (5):

[Formula 5]

$$\frac{\int f \cdot P(f) df}{\int f df} \quad (5)$$

The estimation unit 16 can calculate an intensity f of the average frequency in the first frequency spectrum S1 and an intensity F of the average frequency in the second frequency spectrum S2, based on the above formula (5). Then, the estimation unit 16 may add an average intensity square error between the intensity f of the average frequency and the intensity F of the average frequency to a comparison formula as shown in a formula (6) set forth below and estimate a flow state corresponding to the minimum value of the second frequency spectrum S2 as the flow state of the measurement target fluid. As a result, the fluid measurement apparatus 1 can improve the estimation accuracy.

[Formula 6]

$$\sum_{i}^{N} \left( \frac{F_i}{F_{i+1}} - \frac{f_i}{f_{i+1}} \right)^2 + (\overline{F} - \overline{f})^2 \quad (6)$$

The controller 10 of the fluid measurement apparatus 1 can extract the characteristic component from the frequency spectrum stored as described above. As a result, the fluid measurement apparatus 1 can acquire the characteristic component for each measurement target fluid and thus can improve the convenience. The memory 20 may further store the extracted characteristic component.

The characteristic component of the frequency spectrum may include, for example, the following elements:

(1) Intensity Value of Specific Frequency in Frequency Spectrum

The controller 10 can extract an intensity of a frequency having less noises as a characteristic component of each measurement target fluid. This enables the fluid measurement apparatus 1 to reduce a noise in the measurement result and thus perform appropriate measurement. The intensity of the frequency having less noises may be, for example, an intensity of a frequency at which a product of the frequency f and its intensity P(f) is maximum.

(2) Ratio of Intensity of Specific Frequency in Frequency Spectrum to Intensity of Another Specific Frequency This enables reduction in a noise common to the intensity of each of the frequencies. That is, the estimation unit 16 can improve the estimation accuracy and perform appropriate measurement.

(3) Average Intensity of Frequency Spectrum

This enables the estimation unit 16 to smooth and standardize measurement data and thus facilitates the grasp of a character of an intensity of each flow state. Thus, the estimation unit 16 can easily compare the first frequency spectrum S1 and the second frequency spectrum S2. Further, since the noise common to an intensity of an angular frequency can be reduced, the estimation unit 16 can improve the estimation accuracy.

(4) Value of Intensity Integrated in Specific Frequency Segment of Frequency Spectrum The estimation unit 16 can select and calculate a frequency segment having less noises. This enables the fluid measurement apparatus 1 to reduce the noise in the measurement result and thus to perform appropriate measurement. Further, since the intensity of the frequency spectrum varies according to the flow state, a value obtained by integrating these values are prone to change according to the flow state and thus tends to reflect characteristics of each flow state. That is, the estimation unit 16 can improve the estimation accuracy.

(5) Average Intensity in Specific Frequency Segment of Frequency Spectrum

This enables the estimation unit 16 to smooth and standardize the measurement data and thus facilitates the grasp of the characteristics of intensity for each flow state. Thus, the estimation unit 16 can easily compare the first frequency spectrum S1 and the second frequency spectrum S2. Further, because the estimation unit 16 can calculate selecting a frequency segment that has less noises, the estimation unit 16 can perform calculation reducing the influence of a noise. That is, the estimation unit 16 can improve the estimation accuracy.

(6) Intensity Variance in Specific Frequency Segment of Frequency Spectrum

This enables the estimation unit 16 to calculate reducing the influence of a noise and thus to perform appropriate measurement.

(7) Change in Value of (2) in Frequency Spectrum in Segment from Specific Time t1 to Another Specific Time t2

This enables the estimation unit 16 to estimate further based on a change in a time direction. That is, the estimation unit 16 uses more information for the estimation of the flow rate and thus can improve the estimation accuracy.

The characteristic component as described above is not limited to the above values but may be a parameter that simply enables the comparison between the first frequency spectrum S1 and the second frequency spectrum S2. For example, the characteristic component may be a shape of a specific segment in a power spectrum.

Further, the generator 12 can subdivide the beat signal according to small predetermined times and generate a frequency spectrum in each predetermined time. Thus, a three-dimensional frequency spectrum indicating the passage of time may be prepared. The fluid measurement apparatus 1 may extract the characteristic components from such a three-dimensional frequency spectrum. This enables an estimation of the flow state, based on a transition tendency of the characteristic component according to a change of the flow state. That is, the characteristic components of the power spectrum do not necessarily need to have the same transition tendency, and the flow state can be estimated when the transition tendencies of the entire power spectrum is determined to be the same or similar to one another. Thus, the usefulness of the fluid measurement apparatus 1 can be improved. Further, since the amount of information that can be used for the estimation increases, the fluid measurement apparatus 1 can improve the estimation accuracy.

The extraction of the characteristic components as described above may be used individually or as a combination of two or more thereof. Further, the characteristic components can be used in step S4, which will be described later by way of example.

Next, the estimation unit 16 estimates the flow state of the fluid A, based on a result of the comparison in step S4 (step S5), and then ends an operation illustrated in FIG. 3. The flow state of the fluid A estimated in step S5 may be, for example, at least one of the flow velocity and the flow rate of the fluid A. The estimation unit 16 can estimate the flow state corresponding to the characteristic component S2$c$ of the second frequency spectrum S2 the same as or approximates to the characteristic component S1$c$ of the first frequency spectrum S1 as the flow state of the measurement target. A range in which the estimation unit 16 determines that the characteristic component S1$c$ and the characteristic component S2$c$ approximate to each other may be appropriately determined by the user.

Figure 7:
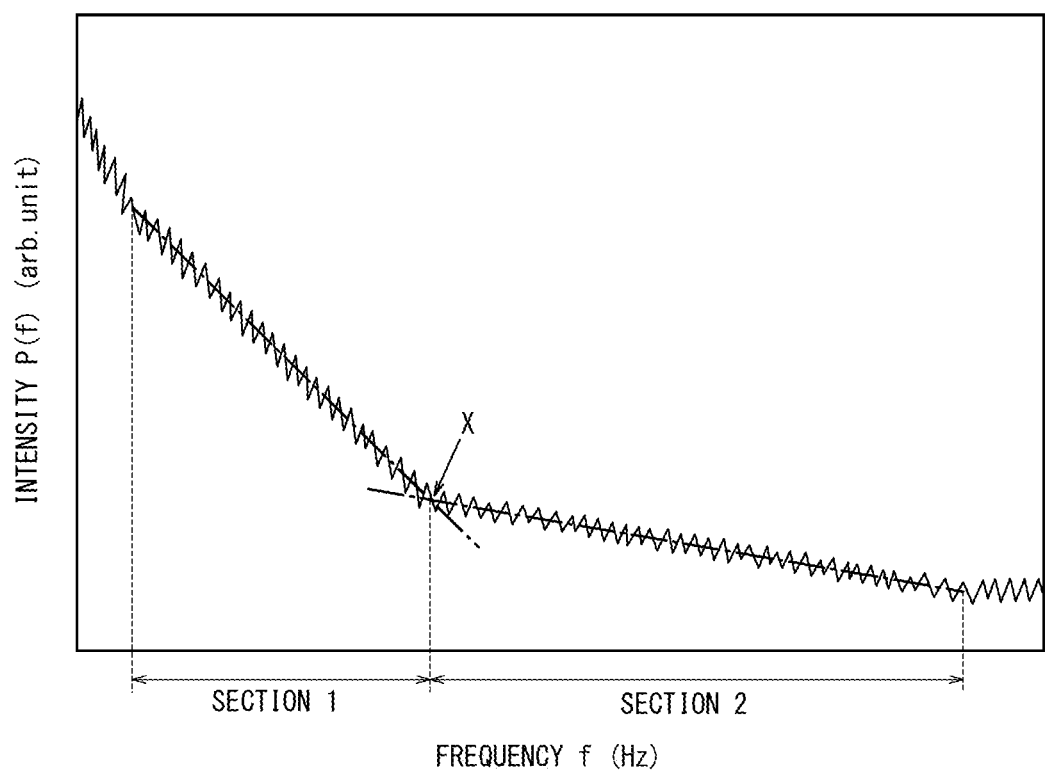
FIG. 7 is a diagram for explaining a principle of fluid measurement according to an embodiment.
Figure 8:
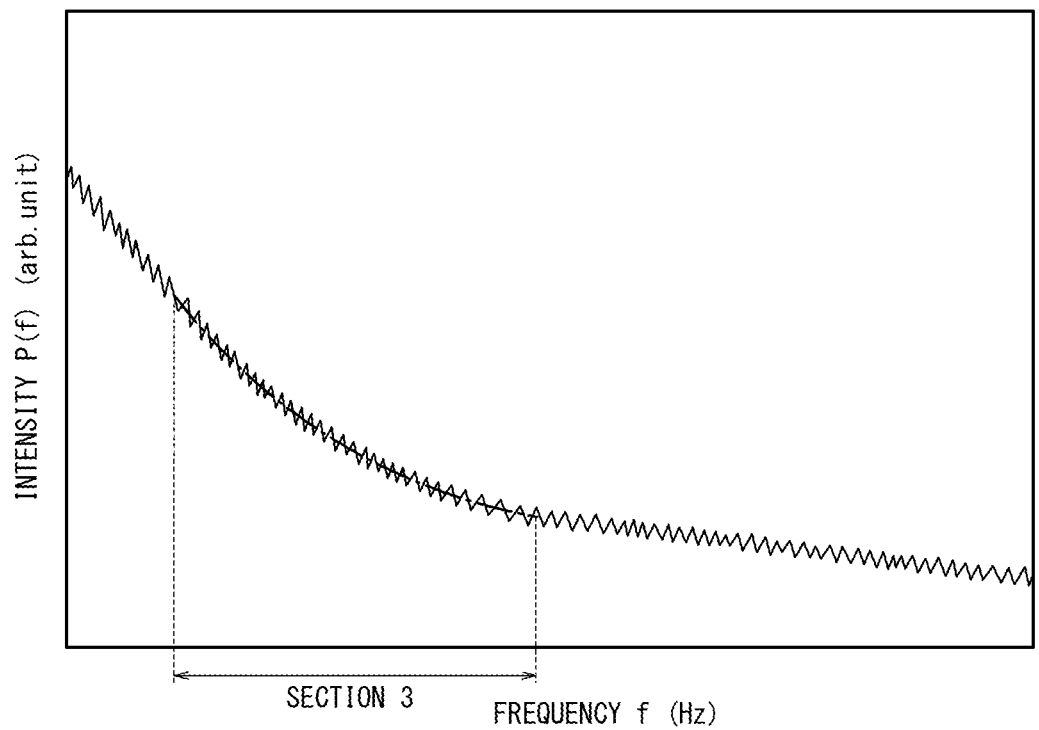
FIG. 8 is a diagram for explaining a principle of fluid measurement according to an embodiment.

The estimation unit 16 may estimate the flow state, based on a shape of a curve in the specific frequency segment of the frequency spectrum. FIG. 7 and FIG. 8 are diagrams for explaining such an estimation method. The concept of the curve of the frequency spectrum includes a straight line. Hereinafter, the method will be described. The shape of the spectrum is, for example, a curve connecting maximum values of the intensities of the respective frequencies, a curve connecting intermediate values of the intensities, or the like. In other words, it is a set of the maximum values of the intensities of the respective frequencies or a set of the intermediate values.

The estimation unit 16 may estimate the flow state by performing bilinear approximation on the first frequency spectrum S1. First, the estimation unit 16 performs linear approximation from any frequency on a low frequency side in a direction toward a high frequency side (e.g., a segment 1 in FIG. 7). The linear approximation may be performed until a degree of approximation has deteriorated. Here, whether the degree of approximation has deteriorated may be determined by, for example, a chi-square test. In particular, when a value obtained by dividing the chi-square value by a degree of freedom exceeds a specific threshold value, it can be considered that the degree of approximation has deteriorated. Then, the estimation unit 16 performs linear approximation in the low frequency direction from any frequency on the high frequency side different from an end point of the first segment (e.g., a segment 2 in FIG. 7). The linear approximation may also be performed until the degree of approximation has deteriorated, in a manner similar to the segment 1. Then, the estimation unit 16 can calculate an intersection of two straight lines (a point X in FIG. 7) as a specific frequency f.

Next, the estimation unit 16 performs the bilinear approximation also on the second frequency spectrum S2. The approximation method may be the same as that performed on the first frequency spectrum S1, and the estimation unit 16 can calculate the specific frequency F in the second frequency spectrum S2.

Then, the estimation unit 16 can estimate the flow state corresponding to the specific frequency F closest to the specific frequency f as the flow state of the measurement target.

The estimation unit 16 may calculate the flow state by approximating with an exponential function. First, the estimation unit 16 approximates a specific frequency segment (e.g., 2 kHz to 20 kHz) in each of the first frequency spectrum S1 and the second frequency spectrum S2 with an exponential function (e.g., a segment 3 in FIG. 8). Next, the estimation unit 16 obtains an exponential function E1 by approximating the first frequency spectrum S1 and obtains an exponential function E2 by approximating the second frequency spectrum S2.

Then, the estimation unit 16 may estimate the flow state corresponding to the exponential function E2 having a parameter most matching a parameter of the exponential function E1 as the flow state of the measurement target.

Here, the characteristic components extracted as exemplified above may be further weighted with the flow state using various learning techniques based on AI (Artificial Intelligence), such as machine learning or deep learning. That is, the fluid measurement apparatus 1 may calculate the flow state of the fluid using various learning techniques.

In particular, the estimation unit 16 can make various learning techniques learn a relationship between a known flow state and the characteristic component of the second frequency spectrum. Then, the estimation unit 16 can calculate the flow state of the measurement target fluid, based on the characteristic component of the first frequency spectrum and the relationship between a flow state weighted by various learning techniques and the characteristic component. Accordingly, the estimation unit 16 can improve the accuracy of comparison between the first frequency spectrum S1 and the second frequency spectrum S2, and thus the fluid measurement apparatus 1 can improve the usefulness.

Note that, for example, in the case of supervised learning, it is simply needs that learning data is the characteristic components exemplified above, and training data is the flow state of the fluid corresponding to the frequency spectrum. The fluid measurement apparatus 1 may estimate the flow state, based on a characteristic component other than the characteristic components mentioned above, using the frequency spectrum as the learning data and the flow state corresponding to the frequency spectrum as the training data. The relationship between the flow state and the characteristic component obtained through learning may be appropriately stored in the memory 20 or the like.

As described above, the characteristic component may be a ratio of an intensity corresponding to at least one specific frequency in the frequency spectrum to an intensity corresponding to at least one frequency other than the specific frequency. The characteristic component may be at least one of an average intensity and a variance of intensities corresponding to a specific segment in the frequency spectrum. Further, the characteristic component may be the shape of the spectrum of the specific segment in the frequency spectrum.

The information regarding the flow state of the fluid A estimated in step S5 may be displayed on various display devices via, for example, the display 40. This enables the user of the fluid measurement apparatus 1 according to the present embodiment to visually recognize the information regarding the flow state of the fluid A.

As described above, the fluid measurement apparatus 1 according to the embodiment can appropriately and accurately estimate the fluid flow state under various conditions related to the fluid flow state. Further, the fluid measurement apparatus 1 can measure the flow state in a relatively wider range than those of conventional laser Doppler flowmeters. That is, the fluid measurement apparatus 1 according to the embodiment can improve the convenience.

Although the disclosure has been described based on the figures and the embodiments, it is to be understood that various changes and modifications may be implemented based on the present disclosure by those who are ordinarily skilled in the art. Accordingly, such changes and modifications are included in the scope of the disclosure herein. For example, functions and the like included in each element may be rearranged without logical inconsistency. A plurality of elements may be combined together, or one element may be subdivided. Each of the above embodiments does not need to be practiced strictly following the description thereof but may be implemented by appropriately combining or partially omitting features.

Further, the embodiments described above are not limited to the realization of the fluid measurement apparatus 1. For example, the embodiments described above may be realized as a fluid measurement method to be executed by the fluid measurement apparatus 1 or a program to be executed by a computer configured to control an apparatus such as the fluid measurement apparatus 1.

A fluid measurement method according to an embodiment includes a step of radiating light to an irradiation target including a fluid, a step of receiving scattered light scattered by the fluid, a step of generating a frequency spectrum based on the scattered light, and a step of estimating a flow state of the fluid based on a characteristic component of the frequency spectrum. The fluid measurement method according to the embodiment generates a first frequency spectrum based on a measurement target fluid and a second frequency spectrum based on the fluid in a known flow state and then compares a characteristic component of the first frequency spectrum and a characteristic component of the second frequency spectrum, whereby the fluid measurement method can estimate the flow state of the measurement target fluid.

A program according to an embodiment causes a computer to perform a step of radiating light to an irradiation target including a fluid, a step of receiving scattered light scattered by the fluid, a step of generating a frequency spectrum based on the scattered light, and a step of estimating a flow state of the fluid based on a characteristic component of the frequency spectrum. The program according to the embodiment causes the computer to generate a first frequency spectrum based on the measurement target fluid and a second frequency spectrum based on the fluid in a known flow state, and then to compare a characteristic component of the first frequency spectrum and a characteristic component of the second frequency spectrum, whereby the program can cause the computer to estimate a flow state of the measurement target fluid.

REFERENCE SIGNS LIST 1 fluid measurement apparatus
10 controller
12 generator
14 acquisition unit
16 estimation unit
20 memory
30 communication interface
40 display
50 driver
60 sensor
62 optical emitter
64 optical detector

The invention claimed is:

1. A fluid measurement apparatus comprising:
an optical emitter capable of radiating light to an irradiation target including a fluid;
an optical detector capable of receiving scattered light scattered by the fluid; and
a controller that includes
a generator configured to generate a first frequency spectrum based on the scattered light,
an acquisition unit configured to acquire a second frequency spectrum based on the fluid in a known flow state, and
an estimation unit configured to estimate a flow state of the fluid based on a characteristic component of the first frequency spectrum,
the controller being configured to estimate a flow state of a measurement target fluid by
causing the generator to generate the first frequency spectrum based on the measurement target fluid and the acquisition unit to acquire the second frequency spectrum, and
then causing the estimation unit to compare a characteristic component of the first frequency spectrum and a characteristic component of the second frequency spectrum.

2. The fluid measurement apparatus according to claim 1, wherein the irradiation target further includes a flow path in which the fluid flows, and the generator is further configured to generate the first frequency spectrum based on interference light caused by interference between the scattered light scattered by the fluid and scattered light scattered by the flow path.

3. The fluid measurement apparatus according to claim 1, wherein the first frequency spectrum is generated from a signal based on the Doppler shift of the scattered light.

4. The fluid measurement apparatus according to claim 1, wherein the characteristic component includes at least one of a value based on an intensity of a specific frequency in the frequency spectrum and a value based on an intensity of a frequency in a specific segment.

5. The fluid measurement apparatus according to claim 4, wherein the characteristic component is a ratio of an intensity corresponding to at least one specific frequency to an intensity corresponding to at least one frequency other than the specific frequency.

6. The fluid measurement apparatus according to claim 4, wherein the characteristic component includes at least one of an average intensity and an intensity variance of the specific segment in the frequency spectrum.

7. The fluid measurement apparatus according to claim 4, wherein the characteristic component is a shape of a specific segment in the frequency spectrum.

8. The fluid measurement apparatus according to claim 7, wherein the estimation unit is configured to use bilinear approximation or exponential approximation in order to determine whether a shape of the first frequency spectrum and a shape of the second frequency spectrum are similar to each other.

9. The fluid measurement apparatus according to claim 1, wherein the estimation unit is further configured to cause a learning technique to determine a relationship between the known flow state and a characteristic component of the second frequency spectrum, and then estimate the flow state of the measurement target fluid based on the characteristic component of the first frequency spectrum and the relationship.

10. The fluid measurement apparatus according to claim 1, wherein the estimation unit is configured to estimate at least one of a flow velocity and a flow rate of the measurement target fluid as the flow state of the measurement target fluid.

11. The fluid measurement apparatus according to claim 1, wherein the optical emitter radiates laser light.

12. A fluid measurement method comprising:
radiating light to an irradiation target including a measurement target fluid;
receiving scattered light scattered by the measurement target fluid;
and
estimating a flow state of the measurement target fluid by generating a first frequency spectrum based on the scattered light from the measurement target fluid and acquiring a second frequency spectrum based on the measurement target fluid in a known flow state, and then comparing a characteristic component of the first frequency spectrum and a characteristic component of the second frequency spectrum.

13. A non-transitory computer-readable recording medium storing instructions, which when executed by a computer, cause the computer to:
radiate light to an irradiation target including a measurement target fluid;
receive scattered light scattered by the measurement target fluid;
and
estimating a flow state of the measurement target fluid by generating a first frequency spectrum based on the scattered light from the measurement target fluid and acquiring a second frequency spectrum based on the measurement target fluid in a known flow state and then comparing a characteristic component of the first frequency spectrum and a characteristic component of the second frequency spectrum.

* * * * *